US007524513B2

(12) United States Patent
Hai-Quan et al.

(10) Patent No.: US 7,524,513 B2
(45) Date of Patent: Apr. 28, 2009

(54) BIOFUNCTIONAL FIBERS

(76) Inventors: Mao Hai-Quan, Block 60 West Coast Crescent, #04-01 West Bay Condominium, 128040 Singapore (SG); Chee Mun Kuan, c/o Johns Hopkins Pte Ltd, 41 Science Park Road, #03-18 The Gemini, Singapore Science Park II, 117610 Singapore (SG); Kam Weng Leong, 10242 Breconshire Rd., Ellicott City, MD (US) 21042

( * ) Notice: Subject to any disclaimer, the term of this patent is extended or adjusted under 35 U.S.C. 154(b) by 333 days.

(21) Appl. No.: 10/481,006

(22) PCT Filed: Jun. 14, 2002

(86) PCT No.: PCT/SG02/00120

§ 371 (c)(1),
(2), (4) Date: Aug. 16, 2004

(87) PCT Pub. No.: WO02/102432

PCT Pub. Date: Dec. 27, 2002

(65) Prior Publication Data

US 2005/0058692 A1  Mar. 17, 2005

(51) Int. Cl.
  *A61K 9/70* (2006.01)
  *A61K 9/52* (2006.01)
  *A61K 9/62* (2006.01)
  *A61K 9/64* (2006.01)
  *B32B 27/12* (2006.01)
  *C12N 5/00* (2006.01)

(52) U.S. Cl. .................. 424/443; 424/1.77; 424/123; 424/457; 514/2; 514/7; 514/23; 528/398; 528/399; 528/422; 528/425; 524/708; 524/710

(58) Field of Classification Search ................ None
  See application file for complete search history.

(56) References Cited

U.S. PATENT DOCUMENTS

| | | | | |
|---|---|---|---|---|
| 5,160,490 | A | 11/1992 | Naughton et al. | 435/284 |
| 5,229,172 | A | 7/1993 | Cahalan et al. | 427/536 |
| 5,874,308 | A | 2/1999 | Kilburn et al. | 435/395 |
| 5,906,828 | A | 5/1999 | Cima et al. | 424/423 |
| 6,045,818 | A | 4/2000 | Cima et al. | 424/423 |
| 6,207,802 | B1 * | 3/2001 | Zsebo et al. | 530/351 |
| 2005/0119450 | A1 * | 6/2005 | Wang et al. | 528/398 |
| 2005/0131200 | A1 * | 6/2005 | Wang et al. | 528/272 |

FOREIGN PATENT DOCUMENTS

EP  0 494 216 B1  5/1997

OTHER PUBLICATIONS

Weimer BC, Walsh MK, Wang X, Influence of poly-ethylene glycol spacer on antigen capture by immbilized antibodies, J. Biochem. Biophys. Methods, 2000, 45:211-219.*

Healy KE, Molecular engineering of materials for bioreactivity, Current Opinion in Solid State and Materials Science, 1999, 4: 381-387.*
GenBank Accession No. CAA35955, Accessed May 12, 2008.*
On-line Medical Dictionary, definition of derivatives and analogs, pp. 1-5, Accessed Jul. 7, 2005.*
Alcorn et al.; "CD34-Positive Cells Isolated From Cryopreserved Peripheral-Blood Progenitor Cells Can Be Expanded Ex Vivo and Used for Transplantation With Little or No Toxicity;" J. Clin. Oncol.; vol. 14, No. 6; Jun. 1996; pp. 1839-1847.
Alcorn et al.; Ex vivo expansion of haemopoietic progenitor cells; Blood Reviews; vol. 10; 1996; pp. 167-176.
Brugger et al. "Reconstitution of Hematopoiesis After High-Dose Chemotherapy by Autologous Progenitor Cells Generated Ex Vivo;" The New England Journal of Medicine; vol. 333, No. 5; Aug. 3, 1995; pp. 283-287.
Dewez et al. "Adhesion of mammalian cells to polymer surfaces: from physical chemistry of surfaces to selective adhesion on defined patterns;" Biomaterials; vol. 19; 1998; pp. 1441-1445.
Dexter et al.; "Conditions Controlling the Proliferation of Haemopoietic Stem Cells In Vitro;" J. Cell. Physiol.; vol. 91; pp. 335-344.
Doheny et al.; "Cellulose as an inert matrix for presenting cytokines to target cells: production and properties of a stem cell factor—cellulose-binding domain fusion protein;" Biochem. J.; vol. 339; 1999; pp. 429-434.
Freed et al. "Biodegradable Polymer Scaffolds for Tissue Engineering;" Biotechnology; vol. 12; Jul. 1994; pp. 689-693.
Gao et al.; "Surface hydrolysis of poly(glycolic acid) meshes increases the seeding density of vascular smooth muscle cells;" Surface Hydrolysis of PGA; 1998; John Wiley and Sons, Inc.
Girton et al.; "Exploiting glycation to stiffen and strengthen tissue equivalents for tissue engineering;" Glycation of Tissue Equivalents; 1999; John Wiley and Sons, Inc.
Girton et al.; "Mechanisms of Stiffening and Strengthening in Media-Equivalents Fabricated Using Glycation;" J. Biomech. Engr.; vol. 122; Jun. 2000; pp. 216-223.
Hoerstrup et al.; "Functional Living Trileaflet Heart Valves Grown In Vitro;" Circulation; Nov. 7, 2000; pp. III-44-49.
Hubbell; "Bioactive biomaterials;" Biochem. Engr.; pp. 123-129.
Hubbell; "Biomaterials in Tissue Engineering;" Biotech; vol. 13; Jun. 1995; pp. 565-576.
Hubbell; "Endothelial Cell-Selective Materials for Tissue Engineering in the Vascular Graft Via a New Receptor;" Bio/Technology; vol. 9; Jun. 1991.

(Continued)

*Primary Examiner*—Anish Gupta
*Assistant Examiner*—Julie Ha
(74) *Attorney, Agent, or Firm*—Greenberg Traurig, LLP

(57) ABSTRACT

The present invention is directed to surface functionalization of polymeric fibers. Surface biofunctionalization is achieved by covalent conjugation of biofunctional igands and/or cell growth factors that are crucial for cell attachment, proliferation and functions. Biofunctional fibers could be fabricated into three-dimensional scaffolds. Polymer fibers described here comprise of biocompatible polymers that are either biodegradable ornon-biodegradable. This patent also describes a series of new biodegradable polyphosphoramidates for the processing of biodegradable fibers. Scaffolds made of non-biodegradable functional fibers could be used for in vitro cell culture (for example, ex vivo cell expansion), while biodegradable functional fibers could be fabricated into tissue engineering scaffolds.

16 Claims, 3 Drawing Sheets

OTHER PUBLICATIONS

Hubbell; "Surface-grafted Cell-binding Peptides in Tissue Engineering of the Vascular Graft;" Annals New York Academy of Sciences; pp. 253-258.

Ito et al.; "Artificial juxtacrine stimulation for tissue engineering;" J. Biomater. Sci. Polymer Edn.; vol. 9, No. 8; 1998; pp. 879-890.

Ito et al.; "Enhancement of the Mitogenic Effect by Artificial Juxtacrine Stimulation Using Immobilized EGF;" J. Biochem.; vol. 121; No. 3; 1997; pp. 514-520.

Jönsson et al.; "Concentration-Dependent Effects of Hematopoietic Growth Factors during In Vitro Expansion of Mouse Stem Cells and Progenitor Cells;" Grown Factors; vol. 14; 1997; pp. 59-66.

L'Heureux et al.; "A completely biological tissue-engineered human blood vessel;" The FASEB Journal; vol. 12; Jan. 1998; pp. 47-56.

Li et al.; "Construction of a Bioengineering Cardiac Graft;" J. of Thoracis and Cardiovascular Surgery; vol. 199, No. 2; Feb. 2000; pp. 368-375.

Long et al.; "Human Hematopoietic Stem Cell Adherence to Cytokines and Matrix Molecules;" J. Clin. Invest.; vol. 90; Jul. 1992; pp. 251-255.

Ma et al.; "Development of an in Vitro Human Placenta Model by the Cultivation of Human Trophoblasts in a Fiber-Based Bioreactor System;" Tissue Engineering; vol. 5, No. 2; 1999; pp. 91-102.

Ma et al.; "Tissue Engineering Human Placenta Trophoblast Cells in 3-D Fibrous Matrix: Spatial Effects on Cell Proliferation and Function;" Biotechnol. Prog.; vol. 15; 1999; pp. 715-724.

Massia et al.; "Vascular Endothelial Cell Adhesion and Spreading Promoted by the Peptide REDV of the IIICS Region of Plasma Fibronectin Is Mediated by Integrin $\alpha_4\beta_1$;" J. Biol. Chem.; vol. 267, No. 20; Jul. 15, 1992; pp. 1409-14026.

Matsuda et al.; "A Hybrid Vascular Model Biomimicking the Hierarchic Structure of Arterial Wall: Neointimal Stability and Neoarterial Regeneration Process Under Arterial Circulation;" J. Thoracis and Cardiovascular Surgery; vol. 110, No. 4, Part 1; Oct. 1995; pp. 988-997.

Mellado-Damas et al.; "Ex-vivo expansion and maturation of CD34-positive hematopoietic prgenitors optimization of culture conditions;" Leukemia Research; vol. 23; 1999; pp. 1035-1040.

Mikos et al.; "Preparation of poly(glycolic acid) bonded fiber structures for cell attachment and transplantation;" J. Biomed. Mat. Res.; vol. 27; 1993; pp. 183-189.

Mooney et al.; "Stabilized polyglycolic acid fibre-based tubes for tissue engineering;" Biomaterials; vol. 17, No. 2; 1996; pp. 115-124.

Naughton et al.; "Molecular and Cellular Controls of Hematopoiesis;" Annals of The New York Academy of Sciences; vol. 554; pp. 126-139.

Naumann et al.; "Tissue Engineering of Autologous Cartilage Transplants for Rhinology;" Am. J. Rhinology; vol. 12, No. 1; Jan.-Feb. 1998; pp. 59-63.

Niklason et al.; "Advances in tissue engineering of blood vessels and other tissues;" Transplant Immunology; vol. 5; 1997; pp. 303-306.

Niklason et al.; "Functional Arteries Grown in Vitro;" Science; vol. 284; Apr. 16, 1999; pp. 489-493.

Oberpenning et al.; "De novo reconstitution of a functional mammalian urinary bladder by tissue engineering;" Nature Biotechnology; vol. 17; Feb. 1999; pp. 149-155.

Petzer et al.; "Differential Cytokine Effects on Primitive ($CD34^+CD38^-$) Human Hematopoietic Cells: Novel Responses to Flt3-Ligand and Thrombopoietin;" J. Exp. Med.; vol. 183; Jun. 1996; pp. 2551-2558.

Petzer et al.; "Self-Renewal of Primitive Human Hematopoietic Cells (Long-Term-Culture-Initiating Cells) in vitro and their Expansion in Defined Medium;" Proc. Natl. Acad. Sci. USA; vol. 93; Feb. 1996; pp. 1470-1474.

Piacibello et al.; "Extensive Amplification and Self-Renewal of Human Primitive Hematopoietic Stem Cells From Cord Blood;" Blood; vol. 89, No. 8; Apr. 15, 1997; pp. 2644-2653.

Pretula et al.; "Preparation of Poly(alkylene H-phosphonate)s and Their Derivatives by Polycondensation of Diphenyl H-Phosphonate with Diols and Subsequent Transformations;" Macromolecules; 1997; vol. 30; pp. 8172-8176.

Roecklein et al.; "Functionally Distinct Human Marrow Stromal Cell Lines Immortalized by Transduction With the Human Papilloma Virus E6/E7 Genes;" Blood; vol. 85, No. 4; Feb. 15, 1995; pp. 997-1005.

Rosenzweig et al.; "Enhanced maintenance and retroviral transduction of primitive hematopoietic progenitor cells using a novel three-dimensional culture system;" Gene Therapy; vol. 4; 1997; pp. 928-936.

Saxena et al.; "Skeletal Muscle Tissue Engineering Using Isolated Myoblasts on Synthetic Biodegradable Polymers: Preliminary Studies;" Tissue Engineering; vol. 5, No. 6; 1999; pp. 525-531.

Shinoka et al.; "Creation of Viable Pulmonary Artery Autografts Through Tissue Engineering;" J. Thoracic and Cardiovascular Surgery; vol. 115, No. 3; pp. 536-544.

Shum-Tim et al.; "Tissue Engineering of Autologous Aorta Using a New Biodegradable Polymer;" Ann Thorac Surg; vol. 68; 1999; pp. 2298-2305.

Sullivan et al.; "Chapter 33: Small-Diameter Vascular Grafts;" Principles of Tissue Engineering; 2nd Edition; 2000; pp. 447-454.

Thomson et al.; "Chapter 21: Polymer Scaffold Processing:" Principles of Tissue Engineering; 2nd Edition; 2000; pp. 251-262.

Turner et al.; "Comparative Adhesion of human haemopoietic cell lines to extracellular matrix components, bone marrow stromal and endothelial cultures;" Brit. J. Haemotol.; vol. 100; 1998; pp. 112-122.

Ueda et al.; "Expansion of human NOD/SCID-repopulating cells by stem cell factor, Flk2/Flt3 ligand, thrombopoietin, IL-6, and soluble IL-6 receptor;" J. Clin. Investig.; vol. 105, No. 7; Apr. 2000; pp. 1013-1021.

von Kalle et al.; "New developments in hematopoietic stem cell expansion;" Curr. Opin. Hematology; vol. 5, No. 1; 1998; pp. 79-86.

Wang et al.; "Modified CelliGen-packed bed bioreactors for hybridoma cell cultures;" Cytotechnology; vol. 9; 1992; pp. 41-49.

Weinberg et al.; "A Blood Vessel Model Constructed from Collagen and Cultured Vascular Cells;" vol. 231, No. 4736; Jan. 24, 1986; pp. 397-400.

Wintermantel et al.; "Tissue engineering scaffolds using superstructures;" Biomaterials; vol. 17, No. 2; 1996; pp. 83-91.

Yagi et al.; "Sustained ex vivo Expansion of Hematopoietic Stem Cells Mediated by Thrombopoietin;" Proceedings of the National Academy of sciences of the United States of America; vol. 96, No. 14; Jul. 16, 1999; pp. 8126-8131.

Zandstra et al.; Cytokine Manipulation of Primitive Human Hematopoietic Cell Self-Renewal; Proceedings of the National Academy of sciences of the United States of America; vol. 94, No. 9; Apr. 19, 1997; pp. 4698-4703.

* cited by examiner

SEQUENCE LISTING

```
<160> NUMBER OF SEQ ID NOS: 6

<210> SEQ ID NO 1
<211> LENGTH: 3
<212> TYPE: PRT
<213> ORGANISM: Artificial
<220> FEATURE:
<223> OTHER INFORMATION: Partial cell adhesion sequence.

<400> SEQUENCE: 1

Arg Gly Asp
1

<210> SEQ ID NO 2
<211> LENGTH: 4
<212> TYPE: PRT
<213> ORGANISM: Artificial
```

```
<220> FEATURE:
<223> OTHER INFORMATION: Exemplary peptide sequence inhibiting
      hematopoietic cell adhesion to fibronectin.

<400> SEQUENCE: 2

Arg Gly Asp Ser
1

<210> SEQ ID NO 3
<211> LENGTH: 6
<212> TYPE: PRT
<213> ORGANISM: Artificial
<220> FEATURE:
<223> OTHER INFORMATION: Exemplary peptide specific for endothlial cell
      attachment

<400> SEQUENCE: 3

Gly Arg Glu Asp Val Tyr
1               5

<210> SEQ ID NO 4
<211> LENGTH: 5
<212> TYPE: PRT
<213> ORGANISM: Artificial
<220> FEATURE:
<223> OTHER INFORMATION: Exemplary peptide for smooth muscle cell
      adhesion.

<400> SEQUENCE: 4

Gly Arg Gly Asp Tyr
1               5

<210> SEQ ID NO 5
<211> LENGTH: 4
<212> TYPE: PRT
<213> ORGANISM: Artificial
<220> FEATURE:
<223> OTHER INFORMATION: Oligopeptide selective for endothelial cell.

<400> SEQUENCE: 5

Arg Glu Asp Val
1

<210> SEQ ID NO 6
<211> LENGTH: 8
<212> TYPE: PRT
<213> ORGANISM: Artificial
<220> FEATURE:
<223> OTHER INFORMATION: Exemplary cell adhesion peptide.

<400> SEQUENCE: 6

Gly Gly Ile Tyr Gly Ser Arg Tyr
1               5
```

BIOFUNCTIONAL FIBERS

GENERAL PURPOSE

The present invention relates generally to surface functionalization of polymeric fibrous scaffolds. More specifically, the invention relates to surface modification of polymer fibers to covalently conjugate biofunctional ligands and/or cell growth factors that are crucial for cell attachment, proliferation and functions. Biofunctional fibers could be arranged into three-dimensional scaffolds. Polymer fibers described here comprise of biocompatible polymers that are either biodegradable or non-biodegradable. Scaffolds made of non-biodegradable functional fibers could be used for in vitro cell culture (for example, ex vivo cell expansion), while biodegradable functional fibers could be fabricated into tissue engineering scaffolds.

BACKGROUND AND PRIOR ARTS

Effective scaffolding is crucial to the success of all tissue-engineering applications and ex vivo cell expansion applications. The design of effective scaffolds has recently been focused on incorporation of specific matrix chemistry, substrate surface configuration and three-dimensional macrostructure design. Polymer scaffolds must possess several key characteristics, including high porosity and surface area, structural strength, and specific three-dimensional shapes, to be useful for tissue engineering applications.

Developing polymeric scaffolds with high porosity, i.e. high surface to volume ratio to provide a large amount of surface for cell attachment has been one of the most active research topics. Several techniques have been established for processing polymers into a porous structure. Most of these methods are based on a class of biodegradable polymers, poly(lactic acid) (PLA), poly(glycolic acid) (PGA) and their polymers (PLGA). Particulate leaching is the first method that has been employed for the fabrication of biodegradable porous foams. This method, however, has less control of the microarchitecture of the pore structure and uniform porosity. An obvious limitation is the difficulties of scaling up of this fabrication technique (Mikos, et al. 1993; Ma, et al. 1998).

Recently, textile technologies are used to fabricate biodegradable woven or nonwoven fabrics as tissue engineering scaffolds (Ma, et al. 1995). Fibers provide a large surface area to volume ratio and therefore are desirable as scaffold materials. The first studied fabric scaffold is a nonwoven mesh made of PGA sutures. Nonwoven PGA fibrous matrix is prepared by entangling fibers or filaments to form an isotropic 3-D matrix structure, leaving a space with a high void volume and a typical porosity in the range of 80-90%. These fibrous matrix lacks of structural stability necessary for the cell culture use. Therefore, several fiber-bonding techniques have been developed to prepare the interconnected fiber networks with different shapes as tissue engineering scaffolds (Thomson, et al. 2000).

Nonwoven fabrics design, compared with biodegradable foams formed by particulate leaching, offers a better control over the scaffold porosity and the fabrication process is more reproducible. These nonwoven mesh scaffolds have achieved good success in several tissue engineering applications, including urinary bladder (Oberpenning, et al. 1999), vascular graft (Niklason, et al. 1999), Trileaflet Heart Valves (Hoerstrup, et al. 2000), cardiac graft (Li, et al. 2000), skeletal muscle (Saxena, et al. 1999), cartilage (Naumann, et al. 1998), etc. Nevertheless, the current available scaffold designs using polymer fibers (mostly non-woven mesh) still pose several limitations.

Firstly, the surface of the fibers used to fabricate scaffolds or matrixes lacks of functional ligands required for cell attachment, proliferation and function. PGA fiber surfaces are not the natural substrate for cell attachment and growth. In almost all the studies mentioned above, the non-woven meshes have been coated by another biodegradable polymer as a binder (e.g. poly-4-hydrobutyrate, PHB) or treated by partial alkali hydrolysis to modify the adsorption of serum proteins onto the surface-hydrolyzed fibers to improve cell attachment and seeding density (Gao, et al. 1998). This process would affect the degradation kinetics of the biodegradable fibers, and is also much less controllable. Moreover, the modified surface adsorbed with serum proteins has no specificity to cell types. Similar approach is taken for non-degradable fibrous matrix. Polyethylene terephtahlate (PET) fibers are partially hydrolyzed and to create enough functionalities on fiber surface to enhance the attachment of the extracellular proteins and therefore improve cell adhesion (Ma, et al. 1999). This patent provides methods to conjugate bioactive signal proteins to the surface of biodegradable fibers and non-degradable fibers.

Secondly, polymer materials used to process biodegradable fibrous scaffolds have been limited to PGA although different bonding materials have been used to stabilize the scaffolds, mostly PLA or PHB. The degradation products of PLA, PGA and PLGA are glycolic acid and lactic acid. They would create an acidic microenvironment at the cell-scaffold interface. Low pH microenvironment is known to be detrimental to maturation of many types of cells and tissue development. Shum-Tim et al. have engineered an ovine pulmonary valve leaflet and the pulmonary arteries from autologous cells using nonwoven PGA mesh (Shum-Tim, et al. 1999). Use of this cell-polymer construct in the systemic circulation resulted in aneurysm formation. This is possibly due to the acidic degradation products or lacking the structural integrity throughout the remodeling process. New biodegradable materials suitable for fiber processing are in great demand to overcome this limitation. This patent also provides a serious of new biodegradable materials that could be processed into fibers and amendable to surface conjugation.

Lastly, nonwoven fabric designs lack of the control of scaffold microarchitecture. Obtaining a uniform porosity is not possible. In addition, nonwoven fabric scaffolds generally have weak mechanical structures. Certain bonding or backing materials are needed to ensure the structural stability. Examples of structural re-enforcing techniques include polypropylene fiber backing for PET meshes (Wang, et al. 1992), solution coating or spray coating of a PLA or PLGA layer (Mikos et al. 1993; Mooney, et al. 1996), sewing with Dexon suture (Niklason et al. 1999), and polyglactin suture (Oberpenning et al. 1999) for PGA meshes. This patent provides methods using textile technologies to provide scaffolds with coherent and ordered structures. Polymer fibers are woven or knitted to form three-dimensional scaffolds with different designed pattern to obtain various degrees of porosity (Wintermantel, et al. 1996), microtopology of the cell culture environment and microdistribution of the functional ligands using surface modified fibers.

This patent describes methods of preparing biofunctional fibers based on non-degradable fibers and biodegradable fibers, describes a serious of new biodegradable materials that could be processed into fibers and amendable to surface conjugation, describes methods of preparing fibrous scaffolds by surface biofunctionalization or using biofunctionalized fibers. These technologies will find wide applications in tissue-engineering and bioprocessing fields. Two specific examples are illustrated below to demonstrate the advantages of this scaffolding technology—stem cell expansion for non-degradable fibrous scaffolds, and vascular graft engineering for the biodegradable scaffolds.

1. Current Stem Cell Expansion Methodologies

A technology for efficient and practical ex vivo expansion of hematopoietic stem cells and progenitor cells would find wide applications in stem cell transplantation and somatic gene therapy. For detailed clinical applications of the expanded haemopoietic progenitor cells, see reference (Alcorn, et al. 1996). Current methodologies for ex vivo stem cell expansion are still far from optimal in achieving high expansion rate and maintaining pluripotency.

The goal of ex vivo expansion is to induce cell division and proliferation of stem cells while maintaining their primary functional phenotypes, namely, their ability to engraft and sustain long-term hematopoiesis. Over the past few years, techniques have become available that allow the extensive proliferation of haemopoietic progenitor cells in ex vivo culture systems. One method of stem cell expansion utilizes an adherent monolayer of stromal cell, which supports the viability of stem cells and early progenitor cells (Dexter, et al. 1977). Briefly, in the first few weeks of culture, a complex adherent layer of stromal cells is laid down. This stromal layer comprises fibroblasts, macrophages, adipocytes, endothelial cells and reticular cells. Hematopoesis can be maintained for months in a long-term bone marrow culture and it is thought that direct adhesive interactions between the hematopoietic cells and various elements of the stroma are crucial to the regulation of primitive hematopoietic cells. This suggests that the complex stromal layer can, to some extent, successfully mimic the unique microenvironment present in the bone marrow. The major advantage of these stromal-based culture systems is their ability to expand the numbers of primitive hematopoietic cells.

Although stromal layer may provide a suitable substrate for hematopoietic cell immobilization and culture, it has a number of limitations. The stromal layer is fragile. Therefore, it requires a rigid substrate on which the layers of stromal cells should be grown in order to maintain the integrity of the stroma. Moreover, cells grown on stroma only have a limited culturing lifetime of about six to eight weeks due to death of the stromal cells. More importantly, the use of stroma for a clinical ex vivo application poses a considerable logistic problem. In most cases, the stromal cells are obtained from the patient to avoid the immuno-rejection. The need to first collect and then grow a layer of the patient's stromal cells before they can be used to culture the hematopoielic cells adds to the time, cost, and complexity of the production of the autologous HPC cells. Moreover the stromal layers are much less defined. It introduces an additional highly variable factor into the culture system. This renders the controlled culturing difficult if reproducible stromal cultures of predictable characteristics are to be obtained. Allogeneic source of stroma, although feasible, is unreliable. The fact that a primary allogeneic stroma has to be irradiated suffers, as any donor-derived tissues would, the potential risks of infection. The quantity to which primary stromal cells can be expanded is limited. Immortalized human stromal cell lines are potentially unlimited in quantity (Roecklein, et al. 1995). However, no allogeneic stromal support is currently available that is suitable for clinical use yet (von Kalle, et al. 1998).

For these reasons, ex vivo culture of HSCs in suspension without stroma a has been actively pursued in recent years. The most widely used method for ex vivo expansion has been a relatively simple liquid suspension culture system supplemented with a combination of a range of cytokines (Hoffman, et al. 1995). The development of HSC in vivo is thought to be regulated, at least in part, by interactions of cytokine receptor signals. Various combinations of cytokines have therefore been studied to obtain the optimal culture conditions for HSC expansion. In particular, stem cell factor (SCF) and Flk-2/Flt-3 ligand (FL) have been used as key cytokines for HSC expansion, because c-Kit and Flk-2/Flt-3, tyrosine kinase receptors for SCF and FL, respectively, have been shown to transduce signals crucial for HSC development. Thrombopoietin (TPO), a ligand for c-Mpl, originally identified as a primary regulator for megakaryopoiesis, has also been shown to stimulate the expansion of primitive hematopoietic cells. A recent study showed that a combination of SCF, FL, TPO, and a complex of IL-6 and soluble IL-6 receptor (IL-6/sIL-6R), was able to induce a significant ex vivo expansion of human hematopoietic stem cells for 7 days. The expanded cells were capable of repopulating in NOD/SCID mice, leading to successful bone marrow engraftment in the recipient animals as measured by considerable numbers of human $CD45^+$ cells 10-12 weeks after transplantation (Ueda, et al. 2000). Simplicity is a major advantage of the cytokine-supplemented suspension culture. In a typical process, $CD34^+$ cells are suspended in culture medium and incubated in an appropriate vessel (tissue culture flasks (Brugger, et al. 1995) or gas-permeable culture bags (Alcorn, et al. 1996; Mellado-Damas, et al. 1999)) for between eight to twelve days. The culture cells can then be harvested with ease and used as required. The medium is preferably serum-free, although a number of studies have used serum-supplemented medium. Serum-free culture allows the researcher to develop a chemically defined medium with known amount of cytokines, therefore the cell expansion process is more controlled and reproducible, and easy to scale up. More importantly, the use of serum free conditions is highly recommended for cell therapy protocols such as employing HPC-derived dendritic cells (DC) and T cells, whose exposure to exogenous antigens can be limited to a minimal level.

While the general protocols for suspension culture are similar, there are a variety of different cytokine recipes developed by various groups. The cytokines most commonly used include a combination of SCF, Flt-3 Ligand, TPO, G-CSF, GM-CSF, IL-3, IL-6, and erythropoietin (Epo). Several recent studies have suggested that SCF, Flt-3 ligand, TPO, and IL-3 might play key roles in the early human hematopoiesis. The combination of these cytokines (especially Flt-3 ligand and TPO) significantly enhanced the amplification of primitive HSCs (Petzer, et al. 1996; Petzer, et al. 1996; Piacibello, et al. 1997; Yagi, et al. 1999). The degree of ex vivo expansion is normally assessed by calculating the fold-increase in total numbers of cells, committed progenitors, $CD34^+$ cells, and LTBMC-IC with respect to the input cells. Routinely, extensive expansion of cell numbers is obtained. Depending on the duration of culture, this can vary from a 30-fold increase in cell numbers from an eight-day culture, up to over 1000-fold increases with longer periods of 14 to 21 days. Similarly, numbers of committed progenitor cells also increase, for example, 41-fold following an eight-day culture, up to 190-fold from a 14-day culture. By repeated feeding of cultures, cell numbers can continue to increase for up to 21 days.

Generally speaking, no stromal influence is incorporated into the suspension culture system, although various combinations of cytokines are utilized to provide the proliferation and differentiation signals that stroma is thought to deliver.

The addition of cytokines is thought to compensate for the absence of stroma-associated support. This represents a major disadvantage when one considers that, in vivo, blood cell production is regulated at a local level by interactions of hematopoietic stem cells with a variety of cell-bound and secreted factors produced by adjacent bone marrow stromal cells. It is unlikely that the cytokine combination currently in use will be adequate substitutes for stroma.

Another limitation of the serum-free suspension culture is the low expansion of the true stem cells, which is measured by long-term-culture-initiating cell (LTC-IC) assay. There is little evidence of significant LTC-IC proliferation, with, at best, maintenance of LTC-IC numbers over the culture period under these conditions. This is probably related to the fact that the current system lacks the unique regulatory microenvironment of bone marrow stroma. Nevertheless, a recent study showed that using a much higher concentration (30-fold higher) of cytokines than for maximal amplification of colony-forming cells, a 60-fold expansion of LTC-ICs from primitive cells has been achieved (Zandstra, et al. 1997). However, other studies have suggested the induction of differentiation of murine stem cells and thus loss of their repopulating ability when high concentration of IL-1, IL-3 and IL-6 are used for the ex vivo expansion (Jonsson, et al. 1997). Down regulation of surface IL-3 receptor in response to the high concentration of soluble IL-3 may have played a role. Immobilized HGFs may alleviate this problem by only providing high concentration of growth factors at the "reaction site".

Recent insights into hematopoietic stem cell biology have demonstrated that the three-dimensional architecture of the culture environment may influence the maintenance of stem cell pluripotency in vitro. Several studies employing three-dimensional devices made of synthetic polymers support the hypothesis that physical topography of bone marrow microenvironments plays an important role in maintaining hematopoietic stem cell viability and pluripotency (Naughton, et al. 1989; Naughton, et al. 1990). These studies show that a 3-D microenvironment supports HPC survival, proliferation and multilineage differentiation. Naughton and Naughton have developed a three-dimensional cell culture apparatus for HSC expansion, in which a stromal support matrix is pre-estabilished and grown on the polymeric mesh surface (Naughton, et al. 1992). An interesting study by Rosenzweig et al. indicates that culturing hematopoietic progenitor cells (HPCs) in a three-dimensional tantalium-coated porous biomaterial structure enhances HPC survival, and preserves primitive $CD34^+$ $CD38^{31}$ cells, even without using hematopoietic growth factors as compared with standard culture techniques. This culture technique improves retroviral transduction of $CD34^+$ cells and LTC-ICs without loss of multipotency (Rosenzweig, et al. 1997).

In summary, other than defining the source of HSCs and developing methods to obtain a purer $CD34^+$ cell source, optimizing the ex vivo culture methodology represents the major challenge for HSC expansion. Considering the various aspects of ex vivo culture of HSCs, we hypothesize that a successful new generation of HSC culture system should include the following key features: (1) a three-dimensional culture device that mimic the microenvironment in the bone marrow stroma, (2) matrix-bound cytokines (including SCF, Flt-3 ligand, TPO, etc.) that mimic the in vivo configuration where these crucial cytokines interact with HSCs in vivo in early hematopolesis, (3) a bioreactor system that is easy to scale up to obtain a clinically acceptable expanded stem cell population.

2 Tissue Engineering of Small Diameter Vascular Grafts

Surgical treatment of vascular disease is now a common medical procedure. However, to date, the use of synthetic polymeric materials is limited to grafts larger than 5-6 mm due to the frequency of occlusion observed with synthetic vessels of smaller diameters. Consequently, significant efforts in the past 15 years have been focused on the development of a small-diameter blood vessel equivalent using tissue-engineering approach. The seeding of synthetic grafts with endothelial cells has been investigated as a means to increase patency, but has been limited by the challenges associated with maintaining effective surface coverage. As an alternative to the use of synthetic materials, two approaches have been taken to create a blood vessel using cell and matrix components. One approach is to create an acellular graft constructed of a material, such as collagen, that would provide the required mechanical properties on implant but would also facilitate remodeling and infiltration of host cells into a cellular vessel (Sullivan, et al. 2000). In this approach, the acellular matrix allografts or xenografts often times require a crosslinking process to provide the requisite mechanical characteristics, and the potential inflammatory response to the acellular grafts still persists. Another approach has gain great attention recently, uses techniques to create a cellular vessel through culture of smooth muscle cells within a biodegradable fibrous matrix and lining the lumen with endothelial cells (Niklason, et al. 1997; Shinoka, et al. 1998; Zund, et al. 1998; Niklason et al. 1999; Shum-Tim et al. 1999).

Weinberg C B and Bell E have first demonstrated in vitro development of a model blood vessel in a porous collagen scaffold in 1986. The remodeled blood vessel has three layers corresponding to an intima, media, and adventitia (Weinberg, et al. 1986). A confluent layer of endothelial cells was grown in culture onto the lumen of a tubular collagen construct consisting of an outer layer of fibroblasts and a middle layer of smooth muscle cells. An external Dacron mesh was used to provide additional mechanical support. However, elastin, the principal arterial-tissue-matrix protein besides collagen, was not present in the model. Matsuda T and Miwa H also created a hybrid construct using a polyureathane scaffold seeded with smooth muscle and endothelial cells (Matsuda, et al. 1995). This construct was shown to remodel in vivo successsfully in a canine model for up to 1 year. It is worth noting that in both of these two designs, a nondegradable polymer support was used to reinforce the strength of the cellular layers.

The state-of-art scaffolding technology in tissue engineering of blood vessel is to employ synthetic nonwoven biodegradable fibrous meshes. Using a partially hydrolyzed PGA nonwoven fabric scaffold, Niklason L E et al. have cultured bovine vessels under pulsatile media flow conditions (Niklason et al. 1999). In this study, vascular biopsy derived aortic smooth muscle cells have been seeded in the scaffold and cultured for 8 weeks, before seeding the endothelial cells in the luminal surface. Pulsatile radical stress is applied to the vessels at 165 beats per minute and 5% radical distention. The remodeled vessels have rupture strengths greater than 2000 mmHg and suture retention strengths of up to 90 grams, and exhibit the beginnings of vascular contractile responses. These engineered arteries have been implanted in miniature swine, and remain patent for up to 3 weeks postimplantation. However, these engineered vessels are also notably lacking in elastin content. In another in vivo blood vessel engineering model, Shum-Tim D et al. have reported a tissue engineered ovine pulmonary artery from autologous cells cultured in a PGA fibrous scaffold (nonwoven mesh) (Shum-Tim et al. 1999). Polyhydroxyalkanoate (PHA) layers have been used to provide the temporary mechanical characteristics of the tubular scaffold as the cells lay down their own extracellular matrix on the PGA surface, which ultimately takes over the structural integrity and biomechanical profile of the engineered tissue. Ovine carotid arteries are harvested, expanded in vitro, and seeded onto 7-mm diameter PHA-PGA tubular scaffolds. The autologous cell-polymer vascular constructs have been used to replace 3-4 cm abdominal aortic segments in lambs. All tissue-engineered grafts remain patent for up to 5 months, and no aneurysms developed by the time of sacrifice. The mechanical strain-stress curve of the TE aorta approaches that of the native vessel. In both studies, scaffolds have been used without any cell adhesive molecules on the surface. A bioadhesive surface would obviously increase the cell seeding efficiency and shorten the time needed for in vitro modeling. This has been difficult to achieve using the current available polymeric materials.

Another key challenge in developing a tissue-engineered blood vessel is to create a construct with the required mechanical properties. Several studies have demonstrated that optimizing the in vitro culture conditions would increase the burst strength of the engineered blood vessel. A few factors that would significantly affect the mechanical characteristics of the remodeled blood vessels include media flow (Ziegler, et al. 1995), ascorbic acid supplement (L'Heureux, et al. 1998)), glycation of the media equivalents (Girton, et al. 1999; Girton, et al. 2000), and particularly, applying pulsatile mechanical stimulus to the cellularized constructs (Niklason et al. 1999). This requires a scaffold with good mechanical strength, which nonwoven-mesh scaffold lacks. As an alternative, additional biodegradable suture, coating or silicon tubing has been used to provide structural integrity and mechanical properties for these non-woven mesh scaffolds (Niklason et al. 1999; Oberpenning et al. 1999; Shum-Tim et al. 1999).

This patent provides biodegradable polymers with functional side chains for the conjugation of adhesion molecules, provides methods of preparing fibrous scaffolds based on biofunctional fibers derived from these polymers.

SUMMARY OF THE INVENTION

1. Biofunctional Fibers—Nonbiodegradable Fiborus Scaffolds for Cell Expansion

We propose a new cell culture system composed of three-dimensional fibrous scaffolds surface-engineered with essential cytokines for hematopoietic stem cells growth and differentiation. The key features include:

(1) The surface of polymer fibers (non-biodegradable) is conjugated with several different growth factors (SCF, FII-3 ligand, TPO, CSFs, etc.) with appropriate spacer and 2-D pattern conducive to the cell attachment and function. Cell adhesion molecules (e.g. RGD sequence (SEQ.ID.NO 1)) may also be conjugated to the fiber surface to facilitate the binding of HSC, and provide the synergy for the interaction between HSC and surface-bound hematopoietic growth factors.

(2) The surface engineered fibers are woven/knitted into a three-dimensional scaffold with various textures (different mesh sizes and patterns) to accommodate cells and facilitate cell-cell interaction.

(3) A bioreactor system can be designed based on this fibrous scaffold. The system can potentially be operated under a continuous condition. The expanded cells are "leached out" from the fibrous scaffolds, and are harvested at any time from the suspension simply by centrifugation.

2 Biofunctional Fibers for Biodegradable Fibrous Scaffolds

This patent provides a new type of biodegradable polymeric fibers processed from polyphosphoramidates (Formula I, see Detailed Description for the structure parameters), which are biodegradable and have good mechanical properties. The side chains of these polymers are conjugated with cell adhesion peptides. The polyphosphoramidates described in this patent are biodegradable. The degradation rate could be adjusted by varying the structure parameters.

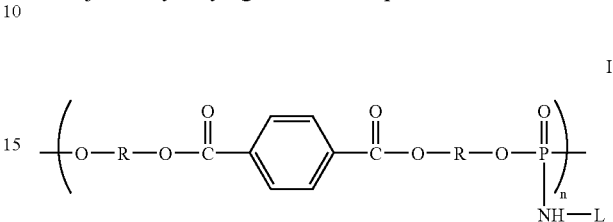

The present patent also provides the methods for preparation of these biodegradable polymers. Biofunctional fibers from these polymers can be obtained by conjugating biofunctional ligands to the side chains of the polymers or by surface modification of the polyphosphoramidate fibers, in later case, polyphosphoramidates carry reactive side chains to allow the further conjugation of biofunctional proteins, peptides or oligosccharides. These biofunctional polymeric fibers could be fabricated into a three-dimensional scaffold by woven/knitting methods. These scaffolds provide optimal supports for cell attachment, proliferation and functions, and allows cells to grow in three dimensions.

Potential Advantages:

1. Nonbiodegradable Biofunctional Fibers for Cell Expansion

This biofunctional fiber design for configuring and constructing cell culture devices provides an optimal microenvironment for hematopoietic stem cell expansion. It also allows various designs of extra-cellular matrices with a reasonable porosity for other applications. The proposed matrix structure allows for a higher immobilized cell density than can normally be achieved by traditional cell culture techniques (flasks or plastic bags).

When surface immobilization and microencapsulation of hematopoietic growth factors and adhesion molecules were incorporated in the three-dimensional culture device, higher expansion rate and better LTC-IC maintenance are expected. This is due to increased contact with HGF immobilized matrix and co-stimulation or synergy of different growth factors/cytokines at a local level, while costs are lowered through controlled release of growth factors. Compare to the conventional culture devices, this newly proposed scaffold has a higher surface area and a higher cell density can be achieved. It also has a low pressure drop across the fibrous structure due to the high porosity, and allows for high mass-transfer of nutrients and oxygen at high cell densities.

The potential applications of this proposed three-dimensional fibrous device are beyond the expansion of hematopoietic stem cells. This biofunctional fibrous scaffold can easily be adapted to the expansion of other growth factor dependent cells, e.g. T-cell expansion and dendritic-cell expansion for adoptive cellular immunotherapy. It is also a useful tool for in vitro studies, such as biochemical signals for growth, differentiation, migration and various extracellular matrix components. These studies are useful in understanding cell-cell interaction: behavior, communication, control, and morphogenesis, and studying the effect of surface properties on cell functions and spatial control of cell micro-organization.

2. Biofunctional Fibers for Biodegradable Fibrous Scaffolds

This patent provides a new type of biodegradable polymeric fibers processed from polyphosphoramidates, which are biodegradable and have good mechanical properties. The side chains of these polymers are conjugated with cell adhesion peptides. These biofunctional polymeric fibers could be fabricated into a three-dimensional scaffold by woven/knitting methods. These scaffolds provide optimal supports for cell attachment, proliferation and functions, and allows cells to grow in three dimensions. The salient and attractive features are:

(1) The scaffold fibers have surface conjugated bioadhesion ligands, which are not available on the PGA/PLA/PLGA fibers. The polyphosphoesters we proposed have available side chains for conjugation of bioadhesive ligands. These ligands could be conjugated through a flexible spacer on the fiber surface. As an alternative, ligands could also be linked to the side chains of the polymer before being processed into fiber. In later case, bioadhesion ligands are distributed throughout the bulk of polymer fiber.

(2) This fibrous scaffold design offers good control of the 3-D porous microarchitecture. The surface engineered fibers or fibers made of bioadhesive polymers are arranged into 3-D scaffolds using nonwoven or woven/knitting techniques. The microporous structures are defined to accommodate cell attachment, facilitate cell differentiation, and guide cell growth and tissue regeneration in three dimensions. This design offers a wide range of suprastructures by chancing fiber diameter, orientation, porosity, and woven and knitting characteristics;

(3) Biofunctional gradient scaffolds can be fabricated through the 3-D arrangement of functional fibers. Biofunctional gradient scaffolds have a single or multiple ligands arranged with a spatial gradient change of their surface concentration. This type of scaffolds is particularly useful in directing tissue growth (e.g. for nerve tissue engineering) or coculture of multiple cell types (e.g. for vascular graft engineering).

(4) The scaffolds have good biocompatibility, mechanical properties, and more steady degradation profile. Polymer fibers are fabricated from new biodegradable polyphosphoesters, tailored to be biocompatible and with no acidic degradation products.

DETAILED DESCRIPTION OF THE PREFERRED EMBODIMENTS

1. Biofunctional Fibers with Adhesion Ligands and Growth Factors

The present invention features a new type of fibers with biofunctional ligands chemically conjugated to the surface. These linkages between ligands and surface are proteolytically stable. These biofunctional fibers are used to construct bioreactors and scaffolds for cell culture and tissue engineering applications. In the following description, stem cell expansion and small-diameter vascular graft tissue engineering are used as specific application examples for the non-biodegradable and biodegradable fibrous scaffolds, respectively. These examples are offered by way of illustration and are not intended to limit the invention in any manner.

2. Surface Conjugation of Adhesion Ligands and Growth Factors

This patent describes methods for the conjugation of biofunctional molecules, including cell adhesion ligands and cell growth factors, e.g. hematopoietic growth factors (HGFs), to the surface of the polymeric fibers via a flexible spacer as shown in FIG. 1. The spacer will ensure enough accessibility of cells to HGFs when interact with the HSCs.

In this design, (1) polymer fibers comprise biodegradable and non-degradable fibers, whereas non-biodegradable fibers comprise fibers selected from polyester fibers (e.g. Dacron), high strength polyethylene fibers, polymethacrylic fibers, polyacrylic fibers, polysulfone fibers, polyurethane fibers, nylon (polyamide) fibers. These fibers are treated with aminolysis or alkali hydrolysis to generate surface carboxyl groups, hydroxyl or amino groups, or treated with argon plasma glow discharge to graft polyacrylic acid segments to the fiber surface. Cell adhesion ligands and growth factors are then conjugated through these functional groups available on the surface (carboxyl groups, hydroxyl groups, amino groups). Biodegradable fibers comprise fibers selected from polyesters fibers (e.g. polyglycolide fibers, poly-4-hydroxybutyrate), polyphosphoester fibers, etc. Polyester fibers are treated with hydrolysis and aminolysis to yield surface carboxyl groups and amino groups, and then conjugated with the adhesion molecules and cell growth factors. A new series of biodegradable poly(terephthalate-co-phosphoramidate)s are designed for this purpose.

(2) Adhesion ligands comprise peptides, saccharides that have specific affinities to the cells that will be cultured in the scaffolds. Examples include cell adhesion peptides derived from collagen, fibronectin, and other extracellular matrix molecules; and saccharide ligands such as galactose, galactosamine and cluster ligands specific for hepatocytes.

(3) Cell growth factors comprise those growth factors that might exert higher function levels when bound to a substrate, e.g. for stem cell culture and expansion, growth factors are selected from one or more of SCF, Flt-3 Ligand, TPO, G-CSF, GM-CSF, IL-3, IL-6, and Epo. The bioactivities of the immobilized hematopoietic growth factors by these bioconjugation techniques are most likely remained. Ito et al. have employed similar bioconjugation methods to immobilize several growth factors, including epidermal growth factor (EGF), insulin, etc. The immobilized growth factors are shown to stimulate cellular functions (Ito, et al. 1998).

(4) Spacer comprises a chain of aliphatic or aromatic groups with a length of 2 to 500 Å. In case that non-specific adhesion should be minimized, a polyethylene glycol spacer with a molecular weight of 3000 to 5000 can be used. Using polyterephthalate as a model surface, Desai N P and Hubbell J A have shown that PEG is effective in reducing protein adsorption and cellular interactions on scaffold surfaces. This is particularly important in the coculture condition (vascular graft), as nonspecific adsorption of serum protein is unfavorable. It would in turn stimulate nonspecific adsorption of cells.

3. Constructing Fibrous Scaffolds from Biofunctional Fibers

A further feature of the provided biofunctional fibers is that they provide a novel approach for constructing fibrous scaffolds with different suprastructures through varying the processing parameters including type of fibers, fiber diameter, orientation, porosity, and weaving/knitting characteristics.

Fiber weaving/knitting techniques can offer a great number of designs for the scaffold microarchitecture. Biofunctional fibers with engineering surface can be arranged into a nonwoven 3-D scaffold with a very high porosity, like the commercially available PGA mesh. An organized and defined pore structure can be obtained by either knitting or weaving into a mesh or 3-D scaffold. Woven scaffold, manufactured with wrap and weft fibers, does not rely on looping of the yarn around a needle and the mesh is therefore more compact. Weaving results in a low-porosity scaffold with greater strength and resistance to deformation compared with the looser structure of the knitted scaffold. Knitted scaffold is much more porous, and has the theoretical advantage of improved handling qualities. Knitted meshes are more prone to stretching. A recent study done using nonwoven and knitted polyethylene terephthalate (PET) fabrics as support matrixes in a human trophoblast cell culture has suggested that spatial characteristics of fibrous matrix are important factors that affect cell adhesion, spatial organization, proliferation, and metabolic functions (Ma, et al. 1999). Although demonstrated in a nonbiodegradable scaffold system, their results suggest that fabric woven/knitting technique could be a valuable tool to provide fibrous scaffolds with well-defined textures.

4. Design and Synthesis of New Polyphosphoramidates for Preparing Biofunctional Fibers The present patent also features a new series of biodegradable polyphosphoramidates, poly(terephthalate-co-phosphoramidate)s, with good mechanical properties and suitable for fiber processing. Terephthalate structure in the backbone provides the mechanical properties needed for fiber processing. Phosphoester side chain provides the functionality for ligand conjugation.

Polyphosphoramidate belongs to a general class of biodegradable polymers called, poly(phosphoester)s. Poly(phosphoester)s define a class of polymers with organic phosphate bond (P—O—C) in the polymer backbone. Interests in polyphosphoesters as biodegradable materials stem from their unique properties including: (1) high structural versatility. (2) favorable physico-chemical properties due to the plasticizing effect of the phosphate bone in the backbone, which would lower the glass transition temperature of the polymer and confer the polymer solubility in common organic solvents, (3) better biocompatibility, (4) availability of functional side groups allowing the chemical linkage of bioadhesive ligands to the polymers. Biodegradable polyphosphoesters with terephthalate groups in the backbone have been developed and shown to have good mechanical properties (Mao, et al. 1999).

The present patents features a series of copolymers of polyterephthalates and polyphosphoramidates, called poly(terephthalate-co-phosphoramidate)s with a general structure shown in Formula I:

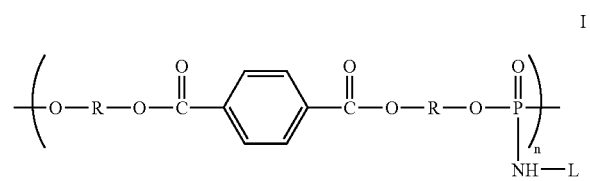

wherein: R is selected form the groups consisting of alkylene, L is selected from the groups consisting of alkyl, aryl, or heterocyclic, and n is 5 to 500.

In a specific embodiment, this invention features a series of poly(terephthalate-co-phosphoramidate)s with a general structure shown in Formula II:

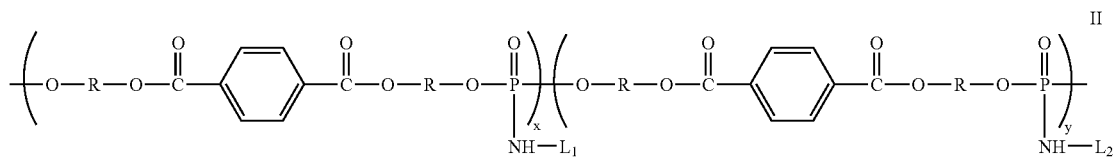

wherein R is the same as described above, $L_1$ and $L_2$ consists of one or two different groups selected from alkyl groups, aryl groups or heterocyclic groups. $L_1$ or $L_2$ can also be selected from any groups that are biofunctional, e.g. cell adhesion peptides, oligosaccharides, etc; x and y are independently selected from integers from 5 to 500.

In a further embodiment, this invention features a series of poly(terephthalate-co-phophoramidate)s with a general structure shown in Formula II, wherein R is the same as described above, $L_1$ or $L_2$ is selected from the alkyl groups, aryl groups or heterocyclic groups with functional groups, e.g. carboxyl groups, amino groups, hydroxyl groups, sulfhydryl groups, etc. These groups can then be used to conjugated proteins, or other biofunctional ligands and growth factors.

In a still further embodiment, the present patent contemplates a process for preparing poly(terephthalate-co-phosphoramidate)s, which comprises a step of reacting a monomer shown in Formula III:

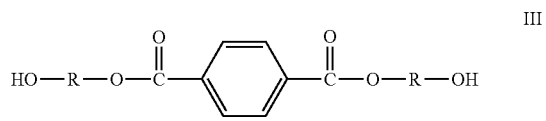

wherein R is defined as above, with diphenyl phosphite to yield a parent polymer, poly(terephthalate o phosphite) with a general structure shown in Formula IV:

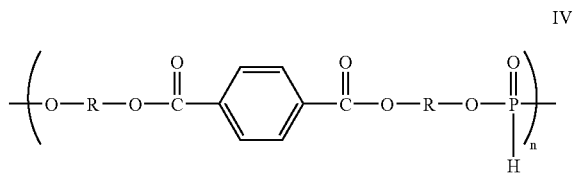

The poly(terephthalate-co-phosphoramidate) is obtained by reacting poly(terephthalate-co-phosphite) with an amine with a formula as: L-$NH_2$, wherein L is defined as above. The general reaction scheme is shown in FIG. 6. in some case, L comprises of groups with protected reactive groups that can be removed efficiently via hydrogenation, e.g. benzoxycarbonyl groups, etc.

In a specific embodiment, this patent concerns a new type of fibers prepared from these biodegradable copolymers. Fibers with various diameters ranging from 15 micrometers to 100 micrometers will be processed through a melt-spin process. Different diameters will facilitate the further design of the microarchitecture for the optimization of cell attachment and tissue growth.

In a still further embodiment, this patent provides two different types of biofunctional fibers. The first one is a type of biodegradable fibers with surface conjugated ligands. In this scheme, fibers are processed using the precursors of the polymers, e.g. poly(terephthalate-co-phosphoramidate)s with reactive side chains, and ligands are conjugated to the fiber surface later. This approach is able to (a) achieve a high ligand density on the fiber surface; (b) modify fiber surface with different ligands easily; and (c) impose minimal infliction on the bulk mechanical properties of the polymers.

The second type of fibers is fabricated after the ligand conjugation to the side chain of the polymer resulting in fibers with functional ligands distributed throughout the biodegradable fibers. In this scheme, fibers are processed using the ligand-conjugated polymers, only when conjugated ligands do not significantly affect the mechanical properties of the polymer and the ligands are stable throughout the fiber fabrication procedure, for example, peptide ligands or oligosaccharide ligands. In some cases, ligand density in the polymer chain will be optimized to accommodate the fiber fabrication procedure; or mixture of the modified and non-modified polymer with different ratio may be used to obtain fibers with required mechanical properties. The advantage of this approach is that the ligand presents during the whole process of tissue regeneration, so that the ligands are displayed on the scaffold surface continuously as it is degraded and remodeled (Hubbell 1999).

5. Biofunctional Fibrous Scaffold for Stem Cell Expansion

In a specific embodiment the present invention concerns a cell culture scaffold composed of biofunctional fibers with a matrix-bound form of HGFs capable of supporting cell attachment and functions. The matrix-bound growth factors could mimic the in vivo cytokine presentation patterns where these cytokines interact with HSCs in the membrane-bound form. Several crucial growth factors involved in the early hematopoiesis, e.g. SCF, Flt-3 ligand, TPO, etc. will be conjugated to the fibers.

Surface attachment of HGFs with maintained bioactivity has been achieved by a number of means. SCF, as well as a number of other growth factors, can act as attachment factors when adsorbed non-specifically to plastic wells, and have been reported to stimulate the proliferation of primitive progenitor cells (Long, et al. 1992). Such a method of immobilization does not ensure the growth factors are presented in the correct conformations, and the surface adsorption of growth factors do not ensure the stability of the growth factors on the surface. It also provides a limited control of the surface configuration and concentration of HGFs. A polar affinity tag might facilitate attachment in the correct orientation but most of the commonly used affinity tags, such as polyhistidine, streptavidin or GST rely on matrices with specific binding groups (e.g. surface with chelating groups with Ni (II) for polyhistidine tag, biotinylated surface for streptavidin tag). These matrices, however, could interfere with the in vitro culture conditions. Doheny J G et al. have reported a chimaera of SCF and a cellulose-binding domain from the xylanase Cex effectively immobilizes SCF on a cellulose surface. The fusion protein retains both the cytokine properties of SCF and the cellulose-binding characteristics of CBDCex. When adsorbed on cellulose, SCF-CBDCex is up to 7-fold more potent than soluble SCF-CBDCex and native SCF in stimulating the proliferation of factor-dependent cell lines (Doheny, at al. 1999; Kilburn, et al. 1999). However, this method involves complicate recombinant protein construction and purification. It is also labor-intensive for conjugation of a number of different HGFs. This patent provides methods of direct conjugation of HGFs to the surface of polymeric fibers as described above. Different type of polymeric fiber may require different chemical schemes for the conjugations.

In a specific embodiment, this invention provides a bioreactor design based on these biofunctional fibers. Three-dimensional porous scaffolds with different micro-topology are constructed through the arrangement of biofunctional fibers using the standard fiber weaving and knitting techniques. The physical topography of microenvironments is believed to play an important role in the maintaining hematopoietic stem cell viability and pluripotency in ex vivo culture. Many investigators consider the presence of stroma indispensable for the maintenance of hematopoietic stem cells (von Kalle et al. 1998), despite the fact that recent evidence suggested that stromal functions can be provided in part by stroma-conditioned medium or HGF supplementation.

In a further specific embodiment, the present patent concerns a biofunctional fibrous scaffold with cell adhesion ligands co-immobilized on the polyemric fibers to provide co-stimulation or synergistic effect of co-immobilized HGFs and cell adhesion ligands. The co-immobilization of HGFs and adhesion molecules can be achieved by random conjugation of a combination of HGFs and adhesion molecules. More attractively, it can also be achieved by design of the weaving and knitting pattern of different biofunctional fibers with each HGF or adhesion molecule attached to one fiber. The later design will provide a controlled pattern of growth factor and adhesion molecule distribution in the local microenvironment, although with limited freedom, due to the size of the fiber (relatively large diameter compared with the cell size).

A wide rage of growth factors is involved in the interaction between stroma and HSCs. Studies have also suggested that adhesion molecules might also contribute to this process. Matrigel, a commercially available artificial extracellular matrix, rich in collagen and fibronectin, has been used to immobilize IL-3 and GM-CSF for growing factor dependent cell lines. In this system, cell adhesion property of the Matrigel might have contributed to the factor dependent cell lines. In this system, cell adhesion property of the Matrigel might have contributed to the factor dependent cell attachment and interaction with the IL-3 and/or GM-CSF. A study by Long et al. suggests that cytokines act together with ECM molecules to anchor stem cells within the microenvironment, thus constitute a developmental signal that synergistically modulates hematopoietic stem cell function (Long et al. 1992). Turner and Murphy have showed that a human hematopoietic cell line adheres to fibronectin coated plastic surface, and this adhesion is completely inhibited by divalent cation chelation and partially inhibited by RGDS (SEQ.ID.NO 2) peptides (Turner et al. 1998).

6. Biofunctional Scaffold for Vascular Graft Tissue Engineering

In one specific embodiment, the present invention describes a biodegradable fibrous scaffold for vascular graft tissue engineering, with a spatial change of multiple ligands through 3-D arrangement of biofunctional fibers. Such a scaffold allows the coculture of two or three different types of cells simultaneously. In this design, two sets of knitted (or nonwoven) fibrous tubular meshes with different diameters will be fixed together as shown in FIG. 2: one set of meshes with surface conjugated GREDVY (SEQ.ID.NO 3) peptide using PEG as a spacer to minimize non-specific adhesion by smooth muscle cells or fibroblasts. Peptide GREDVY (SEQ.ID.NO 3) is specific for endothelial cell attachment, and nonadhesive for smooth muscle cells or fibroblasts, while the second set of meshes with larger diameters has GRGDY (SEQ.ID.NO 4) or other peptides that will promote smooth muscle cells (low selectivity) are arranged at the other layer. Smooth muscle cells (SMCs) will be seeded first into the scaffold, and preferentially attach to the outer set of meshes, since the inner part of scaffold is nonadhesive for SMCs. Several hours or one day later endothelial cells are seeded onto the luminal side of the scaffold. The cells are cocultured for several weeks under pulsatile radical stress condition.

Searching for a highly selective bioadhesion ligand for the fiber surface conjugation could be very challenging. Oligopeptide REDV (SEQ.ID.NO 5) is a sequence identified by Hubbell J A et al. that is highly selective for endothelial cells. They suggest that integrin receptor α4β1 represent a target for selectivity. This receptor presents on the endothelial cells, but not the blood platelets and fibroblasts. The existed adhesion ligand specific for this receptor is a tetrapeptide REDV (SEQ.ID.NO 5). It is present in the III-CS domain of human plasma fibronectin, with a dissociation constant of 2.2×10-6 M and 5.8×106 sites/cell (Massia et al. 1992). This oligopeptide represents a good candidate as a specific ligand for endothelial cells for vascular graft engineering. When a synthetic peptide containing this sequence is immobilized on otherwise cell nonadhesive substrates, endothelial cells attached and spread but fibroblasts, vascular smooth muscle cells do not (Hubbell et al. 1991; Hubbell et al. 1992). Ligands, which are selected for the outer portion of the scaffold, are with less selectivity are from a range of oligopeptides derived from surface adhesion molecule protein, e.g. GRGDY (SEQ.ID.NO 4), etc. (Hubbell et al. 1997). Hereby we propose to conjugate a peptide with a sequence of GREDVY (SEQ.ID.NO 3), to the fibrous scaffold for endothelial cell attachment; and conjugate GRGDY (SEQ.ID.NO 4), GGIYGSRY (SEQ.ID.NO 6) or other cell adhesion peptides to the scaffold for smooth muscle cell attachment (Hubbell et al. 1991; Hubbell et al. 1992). This approach will allow selective seeding of endothelial cells and smooth muscle cells to different zones. Therefore, coculture of the two types of cells would become possible.

Tissue cultures involving more than one cell types present a serious challenge in tissue engineering, (Hubbell 1995). It requires a precise spatial control of bioadhesive ligands with high specificity. Developing scaffolds that can control mammalian cell adhesion to polymer substrate is one of the key issues in tissue engineering, which rests on the ability to direct specific cell types to proliferate, migrate, and express physiology behaviors, in order to yield a cellular architecture and organization performing the functions of the desired tissue. This current design of fibrous scaffolds described in this patent enables selective adhesion of cells on defined patters. This new fibrous scaffold design opens the possibility of controlling placement of cells in a discrete spatial location. It may also allow implementation of new strategies for tissue engineering, by precise manipulations of cell-cell interactions and by improving control on cell function and differentiation (Dewez, et al. 1998).

EXAMPLES

Example 1

Modification of PET Fiber (Nonwoven Mesh) Surface with Lactose

PET mesh (nonwoven, Fiber-cel) is obtained from New Brunswick Scientific Co. (Edison, N.J.). It composed of PET fibers with a diameter of 15 μm, with a porosity of ~90%. Fibra-cel discs were cleaned by rinsing with large amount of water, methanol, hexane, methanol, and water, sequentially. The discs were dried to constant weight. For amination of the fiber surface, the cleaned Fibra-cel discs were incubated with 0.1M ethylenediamine solution in THF for 4 hours at 30° C., and then rinsed with excess amount of THF and deionized water (3 times). The discs were dried to constant weight under vacuum. Amino group content on the fiber surface was measured according to van Delden's method (van Delden C J, et al., J. Biomater. Sci. Polymer Edn, 8(4): 251-268(1996)). Amino group density on PET fiber surface was found to be 0.486 nmol/cm$^2$ with a weight loss of the fiber of 1.14%.

Aminated Fibra-cel discs were incubated in 0.1M sodium borate buffer (pH=9.35) containing 10 mg/ml lactose and 10 mg/ml sodium cyanoborohydride at 40° C. for 48 hours followed by extensive rinsing with 4N NaCl (3 times), deionized water (3 times) and PBS.

Example 2

Culture of Hepatocytes on Surface Modified PET Fibers and Ethoxyresorfin O-dealkylase (EROD) Assay for Cytochrome P450 Activity in Hepatocytes The modified Fibra-cel discs were autoclaved and placed at the bottom of 96-well plate and washed with HepatoZYME-SFM medium. Freshly isolated hepatocytes suspended in HepatoZYME-SFM medium were transferred to the Fibracel discs at a density of $0.5 \times 10^6$ per disc. Cells were then cultured in a humidified atmosphene with 5% $CO_2$. Culture medium was refreshed daily. After 6 days of culture, Fibracels were taken out from the well and washed gently with culture medium for several times to remove the loosely attached hepatocytes. The discs were fixed with 3% glutaraldehyde for 1 h, washed gently with PBS and then post-fixed with osmium tetraoxide for 1 hour. The samples were dehydrated using a graded series of ethanol (25%, 50%, 75%, 95%, and 100%). The discs were fixed on a cover glass and critical point dried for 2 hours. The samples were mounted onto an aluminum stub and sputter coated with gold before viewed under a scanning electron microscope.

In a separate experiment, hepalocytes were cultured in modified Fibra-cel discs for ten days. The medium was replaced with fresh medium containing 39.2 µM 7-ethoxyresorufin, and incubated for two hours. The Fibra-cel discs were viewed on the confocal microscope to evaluate the cytochrome P450 activity in hepatocytes.

Example 3

Synthesis of poly(butylene terephalate-co-butylene phosphoramidate)s (PBPA)

Figure 1:
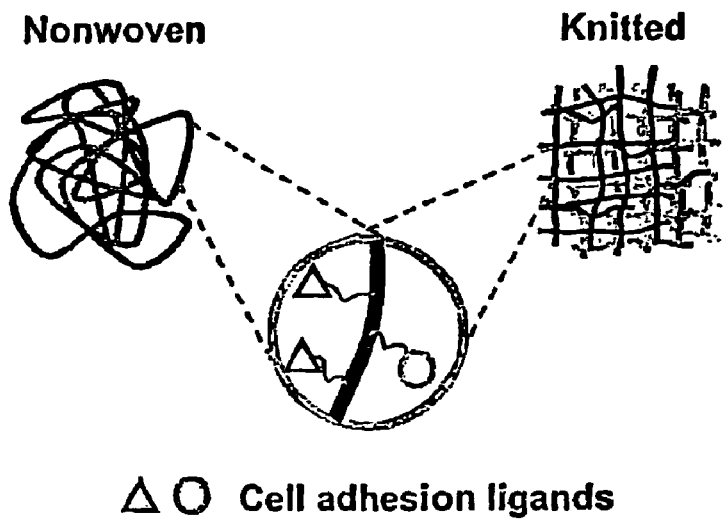
FIG. 1. Schematic description of biofunctional fibers.
Figure 2:
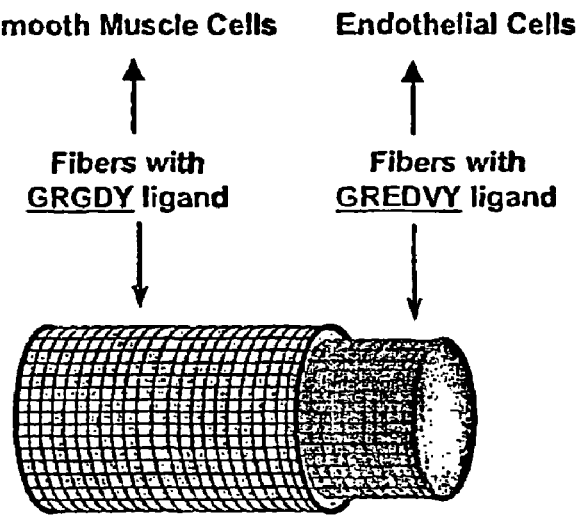
FIG. 2. Schematic description of fibrous scaffolds for vascular graft tissue engineering.
Figure 3:
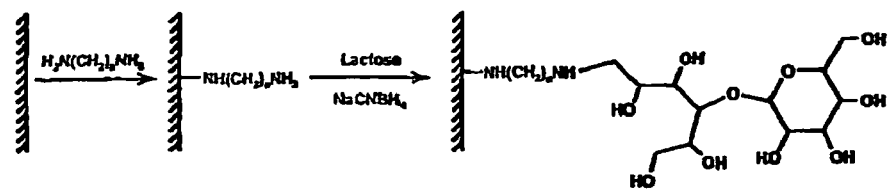
FIG. 3. Surface modification of PET fibers with lactose for hepatocyte cell culture.
Figure 4:
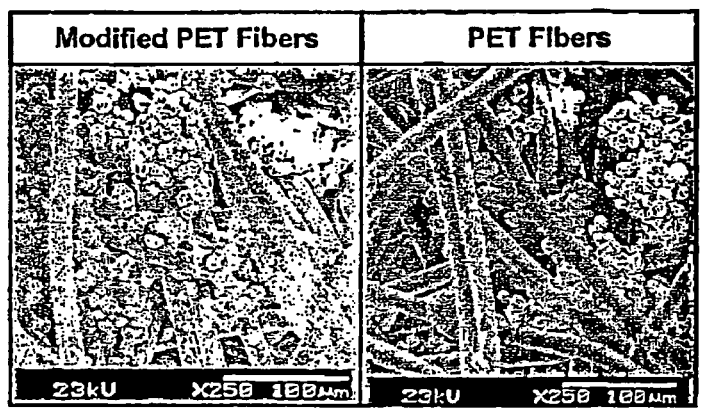
FIG. 4. SEM image of the hepatocytes cultured on modified PET fibers as compared with those on unmodified PET fibers.
Figure 5:
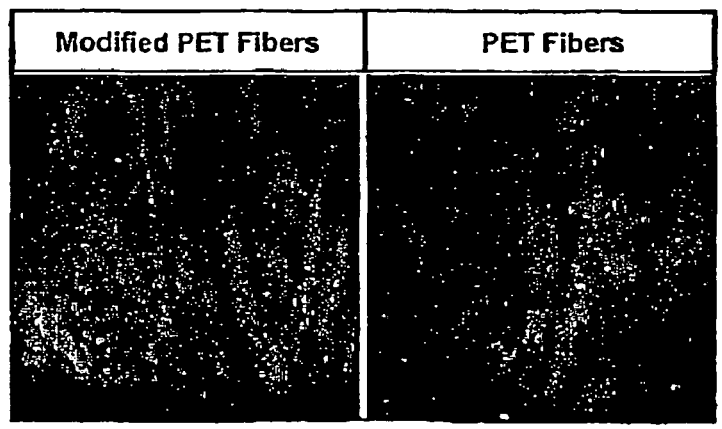
FIG. 5. Ethoxyresorfin O-dealkylase (EROD) assay for cytochrome P450 activity in hepatocytes cultured on modified PET fibers for 10 days. Hepatocytes cultured on unmodified PET fibers server as a control.
Figure 6:
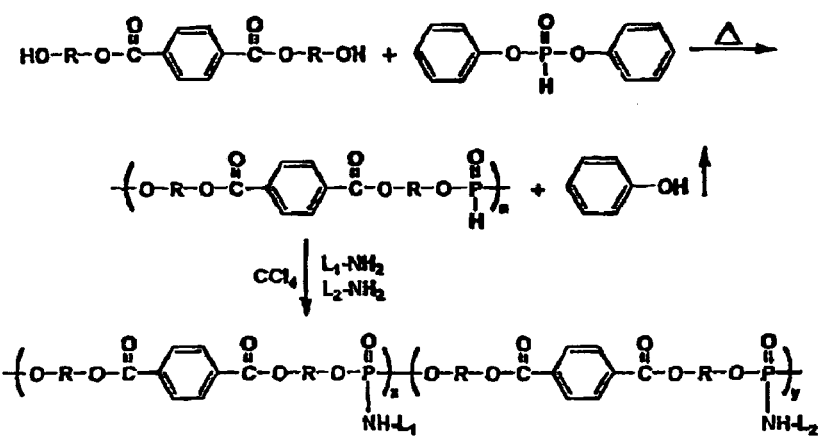
FIG. 6. Synthetic scheme for poly(terephthalate-co-phosphoramidate)s.
Figure 7:
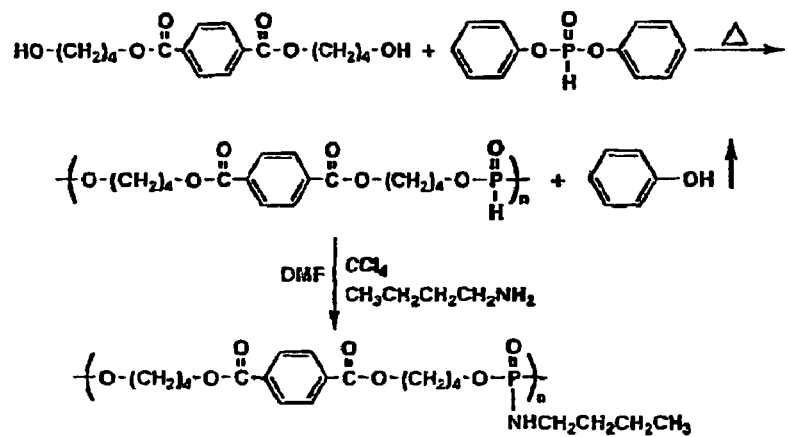
FIG. 7. Synthetic scheme for poly(butylene terephalate-co-butylene phosphoramidate)s.

The reaction scheme is shown in FIG. 7.

Diphenyl phosphite was obtained from Aldrich, and purified by distilling to remove phenol and fractional distillation in the presence of a small grain of sodium. The fraction at 132° C./0.5 mmHg was collected. Bis(hydroxybutyl) terephthalate (BHBT) was obtained from TCl, and purified by recrystallization from methanol twice, and dried under vacuum.

Polycondensation was performed in a vacuum distillation apparatus equipped with a stirring bar and a large Rotaflo stopcock, separating the distillation flask from the condenser, which was attached to the vacuum through a trap immersed in liquid nitrogen. Equimolar amounts of diphenyl phosphite and BHBT were placed and stirred in this apparatus for one hour at 100° C./25 mmHg. Phenol formed during the reaction was continuously distilled off. During the next hour, the temperature was gradually increased to 150° C. and the pressure was decreased to 0.01 mmHg. The viscosity of the reaction mixture increased rapidly to the point that stirring was not possible when the mixture reached 200° C. Poly(butyl terephthalate-co-butyl phosphite) was obtained as white solid (Pretula, et al. 1997).

The above product was dissolved in anhydrous diethylformamide (DMF) gradually to a concentration of 8.9 mmol P—H groups per 10 ml of DMF. To 50 ml of the above solution is added 25 ml of anhydrous $CCl_4$ and 54 mmol of butylamine in 50 ml of DMF using a syringe, followed by addition of 25 ml of anhydrous triethylamine under ice-water (−10~0° C.) bath. The reaction is performed at 0 C for 30 minutes then at room temperature overnight. The resulted solution is concentrated and product is obtained by precipitating in water followed by drying under vacuum.

REFERENCES

Alcorn, M. J. and T. L. Holyoake (1996). "Ex vivo expansion of haemopoietic progenitor cells." *Blood Rev* 10(3): 167-76.

Alcorn, M. J., et al. (1996). "CD34-positive cells isolated from cryopreserved peripheral-blood progenitor cells can be expanded ex vivo and used for transplantation with little or no toxicity." *J Clin Oncol* 14(6): 1839-47.

Brugger, W., et al. (1995). "Reconstitution of hematopoiesis after high-dose chemotherapy by autologous progenitor cells generated ex vivo." *N Engl J Med* 333(5): 283-7.

Dewez, J. L., et al. (1998). "Adhesion of mammalian cells to polymer surfaces: from physical chemistry of surfaces to selective adhesion on defined patterns." *Biomaterials* 19(16): 1441-5.

Dexter, T. M., et al. (1977). "Conditions controlling the proliferation of haemopoietic stem cells in vitro." *J Cell Physiol* 91(3): 335-44.

Doheny, J. G., et al. (1999). "Cellulose as an inert matrix for presenting cytokines to target cells: production and properties of a stem cell factor-cellulose-binding domain fusion protein." *Biochem J* 339(2): 429-34.

Gao, J., et al. (1998). "Surface hydrolysis of poly(glycolic acid) meshes increases the seeding density of vascular smooth muscle cells." *J Biomed Mater Res* 42(3): 417-24.

Girton, T. S., et al. (2000). "Mechanisms of stiffening and strengthening in media-equivalents fabricated using glycation." *J Biomech Eng* 122(3): 216-23.

Girton, T. S., et al. (1 999). "Exploiting glycation to stiffen and strengthen tissue equivalents for tissue engineering." *J Biomed Mater Res* 46(1): 87-92.

Hoerstrup, S. P., et al. (2000). "Functional living trileaflet heart valves grown in vitro [In Process Citation]." *Circulation* 102(19 Suppl 3): 11144-9.

Hoffman, R. and J. Brandt (1995). "Expansion of human hematopoietic progenitor cells in a liquid medium." U.S. Pat. No. 5,409,825.

Hubbell, J. A. (1995). "Biomaterials in tissue engineering." *Biotechnology (N Y)* 13(6): 565-76.

Hubbell, J. A. (1999). "Bioactive biomaterials." *Curr Opin Biotechnol* 10(2): 123-9.

Hubbell, J. A., et al. (1997). "Surfaces having desired cell adhesive effects." European Patent EP494216B1.

Hubbell, J. A., et al. (1991). "Endothelial cell-selective materials for tissue engineering in the vascular graft via a new receptor." *Biotechnology (N Y)* 9(6): 568-72.

Hubbell, J. A., et al. (1992). "Surface-rafted cell-binding peptides in tissue engineering of the vascular graft." *Ann N Y Acad Sci* 665: 253-8.

Ito, Y., et al. (1998). "Artificial juxtacrine stimulation for tissue-engineering." *J Biomater Sci Polym Ed* 9(8): 879-90.

Jonsson, J. I., et al. (1997). "Concentration-dependent effects of hematopoietic growth factors during in vitro expansion of mouse stem cells and progenitor cells." *Growth Factors* 14(1): 59-66.

Kilburn, D. G., et al. (1999). "Compositions and methods for modulating cell proliferation using growth factor-polysaccharide binding fusion proteins." U.S. Pat. No. 5,874,308.

L'Heureux, N., et al. (1998). "A completely biological tissue-engineered human blood vessel." *FASEB J* 12(1): 47-56.

Li, R. K., et al. (2000). "Construction of a bioengineered cardiac graft" *J Thorac Cardiovasc Surg* 119(2): 368-75.

Long, M. W., et al. (1992). "Human hematopoietic stem cell adherence to cytokines and matrix molecules." *J Clin Invest* 90(1); 251-5.

Ma, P. X. and R. Langer (1995). "Degradation, structure and properties of fibrous nonwoven poly(glycolic acid) scaffolds for tissue engineering." *Polymers in Medicine and Pharmacy*. Editor. Mikos A. G. Pittsburgh, Pa., MRS: 99-104.

Ma, P. X. and R. Langer (1998). "Fabrication of biodegradable polymer foams for cell transplantation and tissue engineering." *Tissue Engineering Methods and Protocols*. Eds. M. Yarmush and J. Morgan. Totowa, N.J., Humana Press: 47-56.

Ma, T., et al. (1999). "Tissue engineering human placenta trophoblast cells in 3-D fibrous matrix: spatial effects on cell proliferation and function." *Biotechnol Prog* 15(4): 715-24.

Ma, T., et al. (1999). "Development of an in vitro human placenta model by the cultivation of human trophoblasts in a fiber-based bioreactor system." *Tissue Eng* 5(2): 91-102.

Mao, H.-Q., et al. (1989). "Biodegradable polymers: poly(phosphoester)s." *Encyclopedia of Controlled Drug Delivery*. E. Mathiowitz. New York, Johns Wiley & Sons, Inc.: 45-60.

Massia, S. P. and J. A. Hubbell (1992). "Vascular endothelial cell adhesion and spreading promoted by the peptide REDV of the IIICS region of plasma fibronectin is mediated by integrin $\alpha4\beta1$." *J Biol Chem* 267(20): 14019-26.

Matsuda, T. and H. Miwa (1995). "A hybrid vascular model biomimicking the hierarchic structure of arterial wall: neointimal stability and neoarterial regeneration process under arterial circulation." *J Thorac Cardiovasc Surg* 110(4 Pt 1): 988-97.

Mellado-Damas, N., et al. (1999). "Ex-vivo expansion and maturation of CD34-positive hematopoietic progenitors optimization of culture conditions." *Leuk Res* 23(11): 1035-40.

Mikos, A. G., et al. (1993). "Preparation of poly(glycolic acid) bonded fiber structures for cell attachment and transplantation." *J Biomed Mater Res* 27(2): 183-9.

Mooney, D. J., et al. (1996). "Stabilized polyglycolic acid fibre-based tubes for tissue engineering." *Biomaterials* 17(2): 115-24.

Naughton, B. A., et al. (1990). "A three-dimensional culture system for the growth of hematopoietic cells." *Prop Clin Biol Res* 333: 435-45.

Naughton, B. A. and G. K. Naughton (1989). "Hematopoiesis on nylon mesh templates. Comparative long-term bone marrow culture and the influence of stromal support cells." *Ann N Y Acad Sci* 554: 125-40.

Naughton, G. K and B. A. Naughton (1992). "Three-dimensional cell and tissue culture apparatus." U.S. Pat. No. 5,160,490.

Naumann, A., et al. (1998). "Tissue engineering of autologous cartilage transplants for rhinology." *Am J Rhinol* 12(1): 59-63.

Niklason, L. E., et al. (1999). "Functional arteries grown in vitro." *Science* 284(5413): 489-93.

Niklason, L. E. and R. S. Langer (1997). "Advances in tissue engineering of blood vessels and other tissues." *Transplant Immunology* 5(4): 303-306.

Oberpenning, F., et al. (1999). "De novo reconstitution of a functional mammalian urinary bladder by tissue engineering." *Nat Biotechnol* 17(2): 149-55.

Petzer, A. L., et al. (1996). "Self-renewal of primitive human hematopoietic cells (long-term-culture-initiating cells) in vitro and their expansion in defined medium." *Proc Natl Acad Sci USA* 93(4): 1470-4.

Petzer, A. L., et al. (1996). "Differential cytokine effects on primitive (CD34+CD38−) human hematopoietic cells: novel responses to Flt3-ligand and thrombopoietin." *J Exp Med* 183(6): 2551-8.

Piacibello, W., et al. (1997). "Extensive amplification and self-renewal of human primitive hematopoietic stem cells from cord blood." *Blood* 89(8): 2644-53.

Pretula, J., et al. (1997). "Preparation of poly(alkylene H-phosphonate)s and their derivatives by polycondensation of diphenyl H-phosphonate with diols and subsequent transformations." *Macromolecules* 30(26): 8172-8176.

Roecklein, B. A. and B. Torok-Storb (1995). "Functionally distinct human marrow stromal cell lines immortalized by transduction with the human papilloma virus E6/E7 genes." *Blood* 85(4): 997-1005.

Rosenzweig, M., et al. (1997). "Enhanced maintenance and retroviral transduction of primitive hematopoietic progenitor cells using a novel three-dimensional culture system." *Gene Ther* 4(9): 928-36.

Saxena, A. K., et al. (1999). "Skeletal muscle tissue engineering using isolated myoblasts on synthetic biodegradable polymers: preliminary studies." *Tissue Eng* 5(6): 525-32.

Shinoka, T., et al. (1998). "Creation of viable pulmonary artery autografts through tissue engineering." *J Thorac Cardiovasc Surg* 115(3): 536-45.

Shum-Tim, D., et al. (1999). "Tissue engineering of autologous aorta using a new biodegradable polymer." *Annals of Thoracic Surgery* 68(6): 2298-304.

Sullivan, S. J. and K. G. M. Brockbank (2000). "Small-diameter vascular grafts." *Principles of Tissue Engineering*. Eds. R. P. Lanza, R. Langer and J. Vacanti. San Diego, Calif., Academic Press: 447-454.

Thomson, R. C., et al. (2000). "Polymer scaffold processing." *Principles of Tissue Engineering*. R. P. Lanza. R. Langer and J. Vacanti. San Diego. Calif., Academic Press: 251-262.

Turner, M. L., et al. (1998). "Comparative adhesion of human haemopoietic cell lines to extracellular matrix components, bone marrow stromal and endothelial cultures." *Br J Haematol* 100(1): 112-22.

Ueda, T., et al. (2000). "Expansion of human NOD/SCID-repopulating cells by stem cell factor, Flk2/Flt3 ligand, thrombopoietin, IL-6, and soluble IL-6 receptor." *J Clin Invest* 105(7): 1013-21.

von Kalle, C., et al. (1998). "New developments in hematopoietic stem cell expansion." *Curr Opin Hematol* 5(1): 79-86.

Wang, G., et al. (1992). "Modified CelliGen-packed bed bioreactors for hybridoma cell cultures." *Cytotechnology* 9(1-3): 41-9.

Weinberg, C. B. and E. Bell (1986). "A blood vessel model constructed from collagen and cultured vascular cells." *Science* 231(4736): 397-400.

Wintermantel, E., et al. (1996). "Tissue engineering scaffolds using superstructures." *Biomaterials* 17(2): 83-91.

Yagi, M., et al. (1999). "Sustained ex vivo expansion of hematopoietic stem cells mediated by thrombopoietin." *Proc Natl Acad Sci USA* 96(14): 8126-31.

Zandstra, P. W., et al. (1997). "Cytokine manipulation of primitive human hematopoietic cell self-renewals." *Proc Natl Acad Sci USA* 94(9): 4698-703.

Ziegler, T., et al. (1995). "An endothelial cell-smooth muscle cell co-culture model for use in the investigation of flow effects on vascular biology." *Ann Biomed Eng* 23(3): 216-25.

Zund, G., et al. (1998). "Tissue engineering: a new approach in cardiovascular surgery: Seeding of human fibroblasts followed by human endothelial cells on resorbable mesh." *Eur J Cardiothorac Surg* 13(2): 160-4.

Appendix:

1. Abbreviations
   Stem Cell Expansion:
CBD: cellulose-binding domain
Cex: xylanase Cex
CSF: colony-stimulating factors
DC: dendritic cell
Epo: erythropoietin:
FL: Flt-3Flk-2 ligand
G-CSF: granulocyte colony-stimulating factor
GM-CSF: granulocyte-macrophage colony-stimulating factor
HGF: hematopoietic growth factor
HPC: hematopoietic progenitor cell
HSC: hematopoietic stem cell
IL: interleukin
LTBMC-IC: long-term bone marrow culture initiating cell
LTC-IC: long-term culture initiating cell
RGD: Arg-Gly-Asp
RGDS: Arg-Gly-Asp-Ser
SCF: stem cell factor
SCID: severe combined immunodeficient
sIL-6R: soluble IL-6 receptor
TPO: thrombopoietin
   Vascular Graft Tissue Engineering:
ECM: extracellular matrix
GGIYGSRY: Gly-Gly-Ile-Tyr-Gly-Ser-Arg-Tyr
GREDVY: Gly-Arg-Glu-Asp-Val-Tyr
GRGDY: Gly-Arg-Gly-Asp-Tyr
REDV: Arg-Glu-Asp-Val
PEG: polyethylene glycol
PET: poly(ethylene terephthalate)
PGA: polyglycolic acid
PLA: polylactic acid
PLGA: poly(lactide-co-glycolide)
PPE: polyphosphoester
SMC: smooth muscle cell
TGF: transforming growth factor 2. Related Patents
EP494216B1: Surfaces Having Desirable Cell Adhesive Effects. Inventors: Jeffrey A. Hubbell, Stephen P. Massia, Neil P. Desai. Assignee: Board of Regents The University of Texas System. (Issued/Filed Dates: May 14, 1997/Sep. 27, 1990).

U.S. Pat. No. 5,770,193: Preparation of three-dimensional fibrous scaffold for attaching cells to produce vascularized tissue in vivo. Inventors: Joseph P. Vacanti, Robert S. Langer. Assignee: Massachusetts Institute of Technology Children's Medical Center (Issued/Filed Dates: Jun. 23, 1998/Feb. 28, 1994).

U.S. Pat. No. 5,770,417: Three-dimensional fibrous scaffold containing attached cells for producing vascularized tissue in vivo. Inventors: Joseph P. Vacanti, Robert S. Langer. Assignee: Massachusetts Institute of Technology Children's Medical Center. (Issued/Filed Dates: Jun. 23, 1998/Feb. 28. 1994)

U.S. Pat. No. 5,874,308 (1999): Compositions and methods for modulating cell Proliferation using growth factor-polysaccharide binding fusion proteins. Inventors: Kilburn D G, Humphries K R, Doheny J G, Jervis E, and Alimonti J. (Assignee: University of British Columbia).

U.S. Pat. No. 5,728,581 (1998): Method of expanding hematopoietic stem cells, reagents and bioreactors for use therein. Inventors: Schwartz R, Tucker S N, Chary S R: and Kuo S C. (Assignee: Systemix, Inc. Palo Alto, Calif.)

U.S. Pat. No. 5,948,426 (1999): Method and article to induce hematopoietic expansion. Inventor: Jefferies S R.

U.S. Pat. No. 6,060,052 (2000): Methods for use of Mpl ligands with primitive human hematopoietic stem cells. Inventors: Murray L J, Young J C. (Assignee: SyStemix, Inc. Palo Alto, Calif.).

U.S. Pat. No. 5,912,177 (1999): Stem cell immobilization. Inventors: Turner M L and Murphy W G. (Assignee: Common Services Agency, Edinburgh, GB)

U.S. Pat. No. 5,160,490 (1992): Three-dimensional cell and tissue culture apparatus. Naughton G K and Naughton B A. (Assignee: Marrow-Tech Incorporated, La Jolla, Calif.).

U.S. Pat. No. 5,409,825 (1995): Expansion of human hematopoietic progenitor cells in a liquid medium. Inventors: Hoffman R and Brandt J.

---

The invention claimed is:

1. A biofunctional fiber comprising a biological molecule conjugated to a polyphosphoramidate polymer;
   wherein the polyphosphoramidate is the polyphosphoramidate of Formula I:

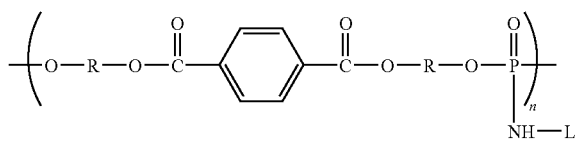

wherein R is an alkylene;
   wherein L is selected from the group consisting of alkyl, aryl, heterocyclic, or biofunctional ligand groups; and
   wherein n is 5 to 500; and
   wherein the biological molecule is selected from the group consisting of: an amino acid sequence, nucleic acid, sugar, oligosaccharide, carbohydrate, lipid, fatty acid, or a combination thereof.

2. A biofunctional fiber comprising a biological molecule conjugated to a polyphosphoramidate polymer;
   wherein the polyphosphoramidate is the polyphosphoramidate of Formula II:

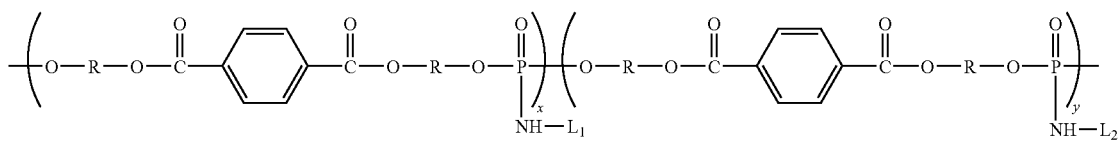

wherein R is an alkylene;
   wherein $L_1$ and $L_2$ each are each independently selected from the groups consisting of alkyl, aryl, or heterocyclic, or biofunctional ligand groups; and
   wherein x and y are independently selected from integers from 5 to 500;
   wherein the biological molecule is selected from the group consisting of: an amino acid sequence, nucleic acid, sugar, oligosaccharide, carbohydrate, lipid, fatty acid, or a combination thereof.

3. The biofunctional fiber of claim 1, comprising two or more distinct biological molecules conjugated to the polymer.

4. The biofunctional fiber of claim 1, wherein the polymer is biodegradable or non-biodegradable.

5. The biofunctional fiber of claim 1, wherein the biological molecule and polymer are conjugated through a covalent bond.

6. The biofunctional fiber of claim 1, wherein the biological molecule and polymer are separated by a spacer.

7. The biofunctional fiber of claim 6, wherein the spacer is between about 2 and 500 angstroms in length.

8. The biofunctional fiber of claim 1, wherein the biological molecule comprises a receptor, ligand, growth factor, proliferation factor, adhesion molecule, differentiation factor, or a molecule modulating signaling or gene expression.

9. The biofunctional fiber of claim 1, wherein the biological molecule comprises at least one of collagen, fibronectin, extracellular matrix molecule, galactose, galactosamine, cluster ligands specific for hepatocytes, SCF, $Flt_3$ Ligand, TPO, G-CSF, GM-CSF, $IL_3$, IL-6, and Epo.

10. The biofunctional fiber of claim 2, comprising two or more distinct biological molecules conjugated to the polymer.

11. The biofunctional fiber of claim 2, wherein the polymer is biodegradable or non-biodegradable.

12. The biofunctional fiber of claim 2, wherein the biological molecule and polymer are conjugated through a covalent bond.

13. The biofunctional fiber of claim 2, wherein the biological molecule and polymer are separated by a spacer.

14. The biofunctional fiber of claim 13, wherein the spacer is between about 2 and 500 angstroms in length.

15. The biofunctional fiber of claim 2, wherein the biological molecule comprises a receptor, ligand, growth factor, proliferation factor, adhesion molecule, differentiation factor, or a molecule modulating signaling or gene expression.

16. The biofunctional fiber of claim 2, wherein the biological molecule comprises at least one of collagen, fibronectin, extracellular matrix molecule, galactose, galactosamine, cluster ligands specific for hepatocytes, SCF, $Flt_3$ Ligand, TPO, G-CSF, GM-CSF, $IL_3$, IL-6, and Epo.

* * * * *